US010174158B2

(12) United States Patent
Prakash et al.

(10) Patent No.: US 10,174,158 B2
(45) Date of Patent: Jan. 8, 2019

(54) METHODS OF PREPARING PARA-XYLENE FROM BIOMASS (71) Applicant: The Coca-Cola Company, Atlanta, GA (US)

(72) Inventors: Indra Prakash, Alpharetta, GA (US); Venkata Sai Prakash Chaturvedula, Mission Viejo, CA (US); Robert M. Kriegel, Decatur, GA (US); Xiaoyan Huang Huang, Marietta, GA (US)

(73) Assignee: The Coca-Cola Company, Atlanta, GA (US)

( * ) Notice: Subject to any disclaimer, the term of this patent is extended or adjusted under 35 U.S.C. 154(b) by 0 days.

(21) Appl. No.: 14/602,610

(22) Filed: Jan. 22, 2015

(65) Prior Publication Data
US 2015/0133627 A1  May 14, 2015

Related U.S. Application Data (63) Continuation of application No. 13/867,407, filed on Apr. 22, 2013, now Pat. No. 8,969,057.

(60) Provisional application No. 61/636,326, filed on Apr. 20, 2012.

(51) Int. Cl.
| C08G 63/183 | (2006.01) |
| C07C 13/20 | (2006.01) |
| C07C 15/08 | (2006.01) |
| C07C 11/167 | (2006.01) |
| C07C 2/50 | (2006.01) |
| C07C 67/08 | (2006.01) |
| C12P 7/62 | (2006.01) |
| C07C 1/20 | (2006.01) |
| C07C 5/27 | (2006.01) |
| C07C 5/367 | (2006.01) |
| C07C 51/265 | (2006.01) |
| C07C 1/207 | (2006.01) |
| C07C 1/24 | (2006.01) |
| C07C 5/46 | (2006.01) |
| C07C 29/132 | (2006.01) |
| C07C 51/16 | (2006.01) |
| C08B 37/00 | (2006.01) |
| C08G 63/78 | (2006.01) |

(52) U.S. Cl.
CPC .............. *C08G 63/183* (2013.01); *C07C 1/20* (2013.01); *C07C 1/2072* (2013.01); *C07C 1/24* (2013.01); *C07C 2/50* (2013.01); *C07C 5/2737* (2013.01); *C07C 5/367* (2013.01); *C07C 5/46* (2013.01); *C07C 11/167* (2013.01); *C07C 13/20* (2013.01); *C07C 15/08* (2013.01); *C07C 29/132* (2013.01); *C07C 51/16* (2013.01); *C07C 51/265* (2013.01); *C07C 67/08* (2013.01); *C08B 37/0087* (2013.01); *C08G 63/78* (2013.01); *C12P 7/62* (2013.01); *C07C 2523/20* (2013.01); *C07C 2529/40* (2013.01); *C07C 2529/44* (2013.01); *C07C 2529/46* (2013.01); *C07C 2529/65* (2013.01); *C07C 2529/67* (2013.01); *C07C 2529/68* (2013.01); *C07C 2601/16* (2017.05); *Y02E 50/17* (2013.01)

(58) Field of Classification Search
CPC ......... C07C 15/08; C07C 1/20; C07C 11/167; C07C 13/20; C07C 2/50; C07C 51/265; C07C 5/2737; C07C 5/367; C07C 11/08; C07C 63/26; C07C 1/2072; C07C 1/24; C07C 2523/20; C07C 2529/40; C07C 2529/44; C07C 2529/46; C07C 2529/65; C07C 2529/67; C07C 2529/68; C07C 2601/16; C07C 29/132; C07C 51/16; C07C 5/46; C07C 67/08; C07C 2101/16; C08B 37/0087; C08G 63/78; C12P 7/62; Y02E 50/17

See application file for complete search history.

(56) References Cited

U.S. PATENT DOCUMENTS

| 2,349,232 | A | 5/1944 | Joshel | |
| 4,423,270 | A | 12/1983 | Pearson | |
| 4,440,871 | A | 4/1984 | Lok et al. | |
| 5,413,681 | A * | 5/1995 | Tustin | B01D 3/009 203/80 |
| 7,199,277 | B2 | 4/2007 | Xu et al. | |
| 2004/0260137 | A1 | 12/2004 | Elomari et al. | |
| 2008/0093777 | A1* | 4/2008 | Sequeira | B29C 47/0023 264/510 |
| 2008/0103340 | A1* | 5/2008 | Binder | C07C 29/60 568/863 |
| 2010/0249474 | A1 | 9/2010 | Nicholas et al. | |
| 2010/0331568 | A1 | 12/2010 | Brandvold | |

(Continued)

FOREIGN PATENT DOCUMENTS

| JP | 2005336217 A * | 8/2005 |
| JP | 2011111400 A | 6/2011 |
| WO | WO 2008/069986 | 6/2008 |

(Continued)

OTHER PUBLICATIONS

Mao et al. Applied Catalysis (1989) 48: 265-277.*

(Continued)

Primary Examiner — Susan M Hanley
(74) Attorney, Agent, or Firm — King & Spalding (57) ABSTRACT Methods or preparing para-xylene from biomass by carrying out a Diels-Alder cycloaddition at controlled temperatures and activity ratios. Methods of preparing bio-terephthalic acid and bio-poly(ethylene terephthalate) (bio-PET) are also disclosed, as well as products formed from bio-PET.

17 Claims, 2 Drawing Sheets (56) References Cited

U.S. PATENT DOCUMENTS

2011/0087000 A1    4/2011   Peters et al.
2012/0171741 A1    7/2012   Peters et al.

FOREIGN PATENT DOCUMENTS

WO    WO 2010/101698          9/2010
WO    WO 2010/151346         12/2010
WO    WO 2012/061272 A2  *    5/2012

OTHER PUBLICATIONS

Gorin et al. Zhurnal Obshchei Khimii (1948) 18: 1069-1076 abstract only.*
Skinner I & EC Fundamentals (1963) 2(3): 168-172.*
English translation of JP 2005-336217 downloaded from the JPO Jun. 24, 2016.*
Paushkin et al. (Nov. Neftekhim. Prod. Protsessy (1971), 19-26 (Year: 1971).*
English translation of Paushkin et al. (Nov. Neftekhim. Prod. Protsessy (1971), 19-26 (Year: 1971).*
PCT International Search Report and Written Opinion for PCT/2013/037546, dated Apr. 21, 2014.
Dolcerawiki, Bio-PET, Mar. 14, 2011 (online).
Xu, et al. *Journal of the Chemical Society, Chemical Communications*, 1992, 17, pp. 1228-1229.
Kvisle, et al., "Transformation of ethanol into 1,3-butadiene over magnesium oxide/silica catalysts", *Applied Catalysis*, 1998, 41 (1), pp. 117-131.
Berak, et al., "Synthesis of butadiene from ethanol II", *Przemysl Chemiczny*, 1962, 41(3), pp. 130-133 (English summary).
Daisuke Nohara et al., "Kinetic study of model reactions in the gas phase at the early stage of coke formation", *Industrial & Engineering Chemistry Research*, vol. 31, No. 1, 1992, pp. 14-19.
Extended European Search Report for EP 13777571.4, dated Apr. 29, 2016.

* cited by examiner

Figure 1

Figure 2

METHODS OF PREPARING PARA-XYLENE FROM BIOMASS

CROSS REFERENCE TO RELATED APPLICATIONS

This application is a continuation of U.S. Ser. No. 13/867,407, which claims the benefit of U.S. Provisional Application No. 61/636,326 filed Apr. 20, 2012. Each application is incorporated herein by reference in their entirety.

FIELD OF THE INVENTION

The invention generally relates to methods of preparing bio-para-xylene (p-xylene) from at least one biomass source, as well as methods for further processing bio-para-xylene produced according to the present invention to provide bio-terephthalic acid and bio-poly(ethylene terephthalate) (PET). The biomass source may be any of a wide variety of starch-, sugar- or cellulose-containing biomass sources from which glucose can be derived.

BACKGROUND

Para-xylene (p-xylene) is an important intermediate in the production of terephthalic acid, a monomer used in the formation of polymers such as poly(ethylene terephthalate) (PET). Yet, traditional methods for the production of p-xylene suffer certain limitations. More specifically, p-xylene is commonly derived from petrochemical source materials having a negative environmental profile and subject to significant price fluctuations. Moreover, p-xylene is commonly prepared from processed petrochemical mixtures containing $C_8$ aromatics, a complex and inefficient process given that p-xylene typically represents only from about 20% to about 25% of the mixture.

Bio-based plastics, or bioplastics, represent a new class of plastics made from biomass source materials, including food (e.g., corn) or non-food materials (e.g., starch-producing plants). Bioplastics offer environmental advantages compared to petroleum-based plastics, including the use of renewable materials and a more limited impact of greenhouse gas emissions. Bioplastics can also normally be produced using the existing manufacturing technology, more often than not using the same reactors and machinery.

PET is among the most commonly used plastics in packaging, particularly in the food and beverage industry. There has been increasing interest in developing PET packaging from biomass. Containers comprising PET derived from bio-based materials, or bio-PET, are disclosed in PCT Publication No. 2009/120457. Commercially available bio-PET packaging contains bio-derived ethylene glycol and petroleum-derived terephthalic acid.

There remains a need for the production of terephthalic acid and p-xylene from renewable biomass sources. There is a further need to provide bio-PET efficiently and cost-effectively using both bio-derived terephthalic acid and bio-derived ethylene glycol.

SUMMARY OF THE INVENTION

Disclosed herein are methods of preparing bio-para-xylene (p-xylene) from at least one biomass source. Methods for further processing bio-para-xylene produced according to the present invention to provide bio-terephthalic acid and bio-poly(ethylene terephthalate) (PET) are also included. The biomass source may be any of a wide variety of starch-, sugar- or cellulose-containing biomass sources from which glucose can be derived.

In one embodiment, synthesis of bio-p-xylene from at least one biomass source comprises (i) deriving glucose from at least one biomass source (referred to herein as bio-glucose); (ii) converting bio-glucose to biomass-derived ethanol (referred to herein as bio-ethanol); (iii) converting a first portion of bio-ethanol to biomass-derived 2-butene (referred to herein as bio-2-butene), and separately, (iv) converting a second portion of bio-ethanol to biomass-derived 1,3-butadiene (referred to herein as bio-1,3-butadiene); (v) reacting bio-2-butene with bio-1,3-butadiene under Diels-Alder cycloaddition conditions to form biomass-derived 4,5-dimethylcyclohex-1-ene (referred to herein as bio-4,5-dimethylcyclohex-1-ene); (vi) dehydrocyclizing bio-4,5-dimethylcyclohex-1-ene to form biomass-derived ortho-xylene (referred to herein as bio-o-xylene); and (vii) isomerizing bio-o-xylene to form bio-p-xylene.

In another embodiment, synthesis of bio-p-xylene from at least one biomass source comprises (i) deriving bio-glucose from at least one biomass source; (ii) converting bio-glucose to bio-ethanol; (iii) dehydrating a first portion of bio-ethanol to biomass-derived ethylene (referred to herein as bio-ethylene); (iv) converting a second portion of bio-ethanol to biomass-derived hexa-2,4-diene (referred to herein as bio-hexa-2,4-diene); (v) reacting bio-hexa-2,4-diene and bio-ethylene under Diels-Alder cycloaddition conditions to form biomass-derived 3,6-dimethylcyclohex-1-ene (referred to herein as bio-3,6-dimethylcyclohex-1-ene); and (vi) dehydrocyclizing bio-3,6-dimethylcyclohex-1-ene to form bio-p-xylene.

The rates of the Diels-Alder cycloadditions are optimized by controlling the temperature of the reaction and activity ratio of the reactants. Specifically, reaction rate is increased through the use of high temperatures and a high activity ratio of diene to dienophile.

The bio-p-xylene prepared by the methods described herein can be further oxidized to provide bio-terephthalic acid. The bio-terephthalic acid can be condensed with biomass-derived ethylene glycol (referred to herein as bio-ethylene glycol) to provide a bio-PET polymer in which both the terephthalic acid component and the ethylene glycol component of the polymer are formed from biomass source material. The bio-PET polymer can be made into a bio-PET resin, which can then be formed into a food or beverage container or product.

The disclosure may be understood more readily by reference to the following detailed description of the various features of the disclosure and the examples included therein.

DETAILED DESCRIPTION

The bio-glucose starting material for the methods of the present invention is obtained, or derived, from at least one biomass source. In some embodiments, two or more biomass sources are used to derive bio-glucose. A biomass source is any natural plant material or plant-derived material that contains starches (i.e. polysaccharides), including starch-containing plant material, sugar-containing plant material and cellulose-containing plant material. Starch-containing plant materials include, but are not limited to, corn, maize, sorghum, barley, wheat, rye, rice, millet, barley, potato, sugarcane, sugar beet, tubers, soybeans or combinations thereof. Sugar-containing plant materials include, but are not limited to, molasses, fruit materials, sugar cane, sugar beet or combinations thereof. Cellulose-containing material include, but are not limited to, wood, plant materials or combinations thereof. In one embodiment, the starch-containing plant material is sugarcane. corn. The plant material may comprise any part of the plant, including but not limited to the root, stems, leaves or combinations thereof.

Conversion of Bio-Glucose to Bio-Ethanol

Both of the Diels-Alder routes to bio-p-xylene described herein rely on the production of bio-ethanol from bio-glucose:

Scheme 1.

glucose → ethanol

The process of converting bio-glucose into bio-ethanol involves the transformation of the sugars of the biomass source material into a distilled pure bio-ethanol product. Various processes and methods for producing bio-ethanol are well known to those of skill in the art. Bio-ethanol production includes at least the following method steps: (1) milling, (2) liquefaction, (3) saccharification, (4) fermentation and (5) distillation. In some instances, certain steps, such as saccharification and fermentation, can be carried out simultaneously.

Milling can be done either wet or dry. Dry milling is the most common process, and involves grinding whole plant matter into meal and formation of a slurry. Wet milling includes various soaking steps to soften grains and separate the soluble starches from the germ, fiber and protein components. Regardless of whether dry or wet milling is performed, the resultant starch-containing material is mixed with water and an alpha-amylase and heated to temperatures from about 180° C. to about 190° C. The slurry then undergoes primary liquefaction in a higher pressure and temperature environment (such as a pressurized jet cooker at 221° F.) before cooling by an atmospheric or vacuum flash condenser. Secondary liquefaction can optionally be performed after primary liquefaction, and involves maintaining the slurry at a temperature 180° C.-190° C. for an extended period of time (e.g. 1-2 hours) to allow the amylase to break down the starch into short chain dextrins. Saccharification can be performed separately or simultaneously with fermentation. Generally the processes are conducted simultaneously. After liquefaction is complete, the mixture (now referred to as "mash") is treated with the enzyme glucoamylase to break down dextrins into simple sugars. An ethanol-producing microorganism is also added to the mash to convert the glucose to ethanol and carbon dioxide. Once saccharification and fermentation are complete, the mash is distilled to isolate the ethanolic fraction from the mash. The ethanolic fraction often contains minor quantities of water, which can be removed by running the ethanolic fraction through molecular sieves to provide 200-proof (anhydrous) ethanol.

The ethanol-producing microorganism can be yeast or bacteria. Ethanol-producing yeast include, but are not limited to, bacteria from the genus *Saccaromyces*. In one embodiment, the ethanol-producing yeast is *Saccaromyces cerevisae*.

In another embodiment, ethanolic-producing bacteria are from the genus *Zymomonas*, such as, for example *Zymomonas mobilis*.

Conversion of Bio-ethanol to Bio-2-Butene

Bio-ethanol can be converted into bio-2-butene by methods known to those skilled in the art according to the following scheme:

Scheme 2.

ethanol → 2-butene

In one embodiment, bio-ethanol is mixed with diethyl ether and treated with an aluminoborate B-C1 catalyst pretreated at 573K at a temperature between 523K-573K (Xu, et al. *Journal of the Chemical Society, Chemical Communications*, 1992, 17, pages 1228-1229).

In another embodiment, bio-ethanol is converted into bio-2-butene according to the method of Manzer, et al., described in PCT Int. Appl. Publication No. WO 2008/069986. Briefly, vaporous ethanol, either directly from the distillation process or revaporized, is contacted with at least one basic catalyst at a temperature from about 150° C. to 500° C. and a pressure from about 0.1 MPa to about 20.7 MPa to produce a mixture of water and butanols, predominantly 1-butanol.

The basic catalyst can be either a homogeneous or heterogeneous catalyst. Homogenous catalysts include, but are not limited to, alkali metal hydroxides. Basic catalysts include, but are not limited to metal oxides, hydroxides, carbonates, silicates, phosphates, aluminates and combinations thereof. In some embodiments, basic catalysts are metal oxides of one of the following metals: cesium, rubidium, calcium, magnesium, lithium, barium, potassium and lanthanum. In certain embodiments, the basic catalyst can be supported by a catalyst support. Catalyst supports include, but are not limited to, alumina, titania, silica, zirconia, zeolites, carbon, clays, double-layered hydroxides, hydrotacites and combinations thereof.

The base catalyst may further contain a catalyst additive or promoter than enhances the efficiency of the catalyst. Promoters include, but are not limited to, Group 8 metals, as well as copper and chromium.

The catalytic conversion of bio-ethanol to water and bio-1-butanol can be performed in either a batch or continuous mode. Suitable reactors include fixed-bed, adiabatic, fluid-bed, transport bed and moving bed.

In some embodiments, the basic catalyst may become fouled and require regeneration. The catalyst is regenerated by contacting the catalyst with a gas selected from the group consisting of air, steam, hydrogen, nitrogen or combinations thereof, at an elevated temperature.

The bio-1-butanol and water mixture can be optionally purified to remove the water, thereby producing a partially-purified product consisting primarily of bio-1-butanol and a small amount of water. In one embodiment, the bio-1-butanol and water mixture can be purified using phase separation followed by distillation to provide a solution with greater than 90% by weight of bio-1-butanol.

The bio-1-butanol and water mixture can then be contacted with at least one acid catalyst to produce bio-2-butene. The reaction can be conducted in either the liquid or vapor phase. The reaction can be performed at a temperature from about 50° C. to about 450° C. In one embodiment, the reaction is carried out at a temperature from about 100° C. to about 250° C.

In one embodiment, the reaction can be carried out at a pressure between atmospheric (about 0.1 MPa) to about 20.7 MPa. In another embodiment, the reaction can be carried out at a pressure from about 0.1 MPa to about 3.45 MPa. The reaction can be performed under inert gaseous conditions, wherein said inert gas is selected from the group consisting of nitrogen, argon and helium.

The acid catalyst can be a homogenous or heterogenous catalyst. Homogenous catalysts include, but are not limited to, inorganic acids, organic sulfonic acids, heteropolyacids, fluoroalkyl sulfonic acids, metal sulfonates, metal trifluoroacetates, compounds thereof and combinations thereof. Homogeneous catalysts useful for the present methods include, but are not limited to, sulfuric acid, fluorosulfonic acid, phosphoric acid, p-toluenesulfonic acid, benzenesulfonic acid, hydrogen fluoride, phosphotungstic acid, phosphomolybdic acid, trifluoromethanesulfonic acid or combinations thereof.

Heterogenous catalysts include, but are not limited to, heterogenous heteropolyacids, natural clay minerals, cation exchange resins, metal oxides, mixed metal oxides, metal salts, zeolites and combinations thereof. For example, the heterogenous catalyst can be a metal salt, including, but not limited to, metal sulfides, metal sulfates, metal sulfonates, metal nitrates, metal phosphates, metal phosphonates, metal molybdates, metal tungstates, metal borates or combinations thereof.

The product of the acid catalysis, bio-2-butene, can be purified from the reaction mixture by methods known to those of skill in the art, including, but not limited to, decantation, filtration, extraction or membrane separation.

Conversion of Bio-ethanol to Bio-1,3-butadiene

Bio-1,3-butadiene can be prepared from bio-ethanol according to the following scheme:

Scheme 3.

ethanol     1,3-butadiene

In one embodiment, bio-ethanol is converted to bio-1,3-butadiene by being passed over a metal oxide catalyst at a temperature from about 400° C. to about 450° C. The reaction produces bio-1,3-butadiene as well as water and hydrogen gas.

In another embodiment, bio-ethanol is passed over a magnesium oxide/silica catalyst in the vapor phase to produce bio-1,3-butadiene. The catalyst can be a mixture of MgO and SiO$_2$. In another embodiment, the catalyst is a mixture of MgO, SiO$_2$ and Al$_2$O$_3$. The catalysts may further comprise CaHPO$_4$ or Ca$_3$(PO$_4$)$_5$.

The reaction can be carried out at a temperature from about 350° C. to about 450° C. or from about 370° C. to about 390° C. Exemplary catalytic conversions of ethanol to 1,3-butadiene are described in Kvisle, et al., "Transformation of ethanol into 1,3-butadiene over magnesium oxide/silica catalysts", *Applied Catalysis*, 1998, 41(1), pages 117-131 and Berak, et al., "Synthesis of butadiene from ethanol II", *Przemysl Chemiczny*, 1962, 41(3), pages 130-133.

The bio-1,3-butadiene can be purified from the reaction mixture by methods known to those of skill in the art, including, but not limited to, decantation, filtration, extraction or membrane separation.

Dehydration of Bio-ethanol to Bio-ethylene

Bio-ethylene serves as the diene in the Diels-Alder cycloaddition with bio-(2E,4E)-hexa-2,4-diene. Bio-ethanol can be dehydrated to form bio-ethylene according to the scheme below:

Scheme 4.

ethanol     ethylene

Methods of preparing ethylene from ethanol are known in the art. Industrial processes for the dehydration of ethanol in a fluidized bed reactor are described in U.S. Pat. No. 4,423,270. The ethanol starting material is obtained from glucose isolated from biomass, as described above.

The dehydration of bio-ethanol can be conducted using any known dehydration catalyst. Dehydration catalysts include, but are not limited to, alumina, silica-alumina, silicoaluminophosphate (SAPO) molecular sieves (U.S. Pat. Nos. 4,440,871 and 7,199,277), metal-substituted aluminophosphates (AlPOs; U.S. Patent Publication No. 2010/0249474) activated clays, zeolites, TiO$_2$/γ-Al$_2$O$_3$, Syndol, sulfuric acid, phosphoric acid, substituted phosphoric acids (described in U.S. Pat. No. 4,423,270). Vaporized bio-ethanol can be passed over the dehydration catalyst.

The dehydration of bio-ethanol to ethylene may proceed by contacting bio-ethanol with a dehydration catalyst in a fluidized bed reactor at a temperature from about 700° C. to about 1000° C. or from about 750° C. to about 900° C.

Conversion of Bio-ethanol to Bio-hexa-2,4-diene

Bio-hexa-2,4-diene serves as the dienophile in the Diels-Alder cycloddition with bio-ethylene. Bio-ethanol can be converted to bio-hexa-2,4-diene according to the scheme below:

Scheme 5.

ethanol (2E,4E)-hexa-2,4-diene)

Methods of preparing hexa-2,4-diene from ethanol are known in the art. The bio-ethanol starting material is obtained from glucose derived from at least one biomass source, as described above.

In one embodiment, bio-ethanol is combed with methyl ethyl ketone (MEK) and passed over a suitable catalyst, for example silica gel impregnated with tantalum oxide (SiO$_2$—Ta$_2$O$_5$), silicamagnesium-tantalum, silica-magnesium-chromium or a Lebedev catalyst.

The reaction can be carried out at a temperature from about 100° C. to about 500° C. or from about 370° C. to about 450° C.

The bio-hexa-2,4-diene can be obtained from the resultant product according to the procedure described in Gorin, et al., *Zhurnal Obshchei Khimii,* 1948, 18, pages 1069-1076.

Diels-Alder Cycloaddition of Buta-1,3-diene and 2-butene

Bio-buta-1,3-diene (the diene) and bio-2-butene (the dienophile) are reacted under appropriate Diels-Alder cycloaddition conditions to produce the [4+2] cycloadduct, bio-4,5-dimethylcyclohex-1-ene, according to the following scheme:

Scheme 6.

2-butene   1,3-butadiene 4,5-dimethylcyclohex-1-ene

Bio-(2E,4E)-hexa-2,4-diene (the diene) and bio-ethylene (the dienophile) are reacted under appropriate Diels-Alder conditions to produce the [4+2] cycloadduct, bio-3,6-dimethylcyclohex-1-ene, according to the following scheme:

Scheme 7.

(2E,4E)-hexa-2,4-diene

+ ethylene →

3,6-dimethylcyclohex-1-ene

The cycloaddition can be carried out in any suitable vessel. In one embodiment, the cyclo addition is carried out in a tube reactor. In another embodiment, the cycloaddition is carried out in a standard pressure vessel.

Efficient reaction times for the methods herein can be accomplished by controlling cycloaddition conditions. Cycloaddition conditions can include temperature, activity ratio, solvent, pressure and run time. In one embodiment, efficient reaction times are accomplished by maximizing the cycloaddition conditions of temperature and activity ratio.

In one embodiment, the cycloaddition is carried out at a temperature from about 100° C. to about 700° C. For example, the cycloaddition can be carried out at a temperature from about 200° C. to about 700° C., from about 500° C. to about 700° C., from about 175° C. to about 300° C. or from about 225° C. to about 300° C.

The activity ratio is defined as moles of diene to moles of dienophile. For example, an activity ratio of 1 corresponds to one mole of diene to one mole of dienophile. In another example, an activity ratio of 25 corresponds to 25 moles of diene to one mole of dienophile. Generally, higher activity ratios result in faster rates of cycloaddition between reactants. Accordingly, the activity ratio of diene to dienophile is at least 2:1, more preferably at least 5:1, more preferably at least 10:1, more preferably at least 15:1, more preferably at least 20:1, more preferably at least 25:1, more preferably at least 30:1, more preferably at least 35:1, more preferably at least 40:1, more preferably at least 45:1, more preferably at least 50:1, more preferably at least 55:1, more preferably at least 60:1; more preferably at least 65:1, more preferably at least 70:1, more preferably at least 75:1, more preferably at least 80:1, more preferably at least 85:1, more preferably at least 90:1, more preferably at least 95:1, more preferably at least 100:1.

Both the temperature and the activity ratio of the cycloaddition can be optimized to provide acceptable reaction times. In one embodiment, the temperature is from about 100° C. to about 700° C. and the activity ratio is from about 2:1 to about 100:1. In another embodiment, the temperature is from about 500° C. to about 700° C. and the activity ratio is from about 50:1 to about 100:1.

The cycloaddition can be carried out at atmospheric pressure or under higher pressures. Generally, higher pressures will accelerate formation of the cycloadduct. The pressure can range from about 100 psi to about 10,000 psi, such as from about 200 to about 8,000 psi, from about 400 to about 6,000 psi or from 600 to 3,000 psi.

The cycloaddition can be carried out in any compatible aqueous or organic solvent. In one embodiment, a polar organic solvent is used. Suitable organic solvents include, but are not limited to, benzene, toluene, dioxane, xylene, nitrobenzene, acetone, chlorobenzene, ethyl ether, cyclohexane, hexane, chloroform, dichloromethane, tetrahydrofuran, ethyl acetate, acetone, dimethylformamide, acetonitrile, dimethyl sulfoxide, formic acid, butanol, isopropanol, propanol, ethanol, methanol or combinations thereof.

The course and completion of the cycloaddition can be monitored by any method known to those skilled in the art. Suitable methods for monitoring the cycloaddition include thin layer chromatography, gas chromatography, high performance liquid chromatography, mass spectroscopy and nuclear magnetic resonance spectroscopy.

One of skill in the art will recognize that the run time for the Diels-Alder cycloaddition described herein will vary based on the reactants, reactant concentration, solvent, temperature and pressure. Accordingly, the run time for the methods described herein can be from about 5 minutes to about 24 hours. For example, the run time can be from about 30 minutes to about 10 hours or from about 2 hours to about 5 hours. The reaction can either be run until all of the reactants have been consumed, or can be halted prematurely to allow for isolation of the cycloadduct.

In one embodiment, the Diels-Alder cycloaddition for bio-buta-1,3-diene and bio-2-butene proceeds under the same conditions (e.g. temperature, activity ratio, solvent, pressure, run time) as the Diels-Alder cycloaddition of bio-(2E,4E)-hexa-2,4-diene and bio-ethylene. It is understood, however, that in other embodiments the conditions for each cycloaddition can be different, i.e. run at different temperatures, with different activity ratios, in different solvents, with different pressures, for different periods of time.

The cycloadducts can be purified by any method known to one of skill in the art, including, but not limited to, filtration, extraction, chromatography, crystallization or membrane separation.

In some embodiments, the Diels-Alder cycloaddition reaction occurs with greater than 50% yield. For example, the reaction may proceed in greater than 60% yield, greater than 70% yield, greater than 80% yield, greater than 90% yield, greater than 95% yield, greater than 97% yield, greater than 98% yield or greater than 99% yield.

Dehydrocyclization/Aromatizing of Diels-Alder Cycloadducts

The Diels-Alder cycloadducts (bio-4,5-dimethylcyclohex-1-ene and bio-3,6-dimethylcyclohex-1-ene) can be dehydrocyclized/aromatized to provide bio-xylenes according to the following scheme:

Scheme 8.

4,5-dimethylcyclohex-1-ene    ortho-xylene 3,6-dimethylcyclohex-1-ene    para-xylene Aromatization of bio-4,5-diemethylcyclohex-1-ene provides bio-ortho-xylene (bio-o-xylene). Aromatization of bio-3,6-dimethylcyclohex-1-ene provides bio-para-xylene (bio-p-xylene).

Methods of dehydrocyclizing/aromatizing are known in the art. In one embodiment, the Diels-Alder cycloadduct is aromatized by contacting the cycloadduct with a dehydrocyclization catalyst in the presence of a $H_2S$ modifying agent. The $H_2S$ modifying agent can be any compound that will form $H_2S$ under dehydrocyclization conditions. Sulfur-bearing compounds that are useful as modifying agents are provided in U.S. Pat. No. 3,428,702, and include, but are not limited to, ally sulfide, benzoyl sulfide, benzyl disulfide, benzyl sulfide, 2-methyl-1-butanethiol, 3-methyl-1-butanethiol, 2-methyl-2-butanethiol, tert-octanethiol, butyl disulfide, butylsulfide, 1,2-ethanedithio, ethanthiol, ethylene sulfide, ethyl disulfide, furfuryl mercaptan, 1-heptanethiol, 1-hexanethiol, isoamyl disulfide, isoamyl sulfide, isobutyl sulfide, methyl disulfide, methyl sulfide, 2-naphthalenethiol, 1-naphthalenethiol, 1-pentanethiol, phenyl disulfide, 1-propanethiol, 2,2'-thiodiethanol, thiophene, acetyl disulfide, benzenesulfonic acid, o-bromo-benzenesulfonic acid, p-bromo-benzenesulfonic acid, o-formyl-benzenesulfonic acid, methyl benzenesulfonic acid, benzyl sulfoxide, butyl sulfoxide, 2,2'-dithiophene, butyl sulfate, butyl sulfonate, butyl sulfone, butyl sulfoxide, dithiocarbamic acid, thiol-carbamic acid, thiono-carbamic acid, tri-thio-carbonic acid, dithiol-carbonic acid, cetyl sulfate, dodecyl sulfate, 1,2-ethanedisulfonic acid, ethionic anhydride, ethyl sulfite, ethyl sulfone, ethyl sulfoxide, ethyl sulfuric acid, methanethiol, methyl sulfoxide, 2-bromothiophene, 2-chlorothiophene, 2,5-dimethylthiophene, 2,5-diiodothiophene, 2,3-dimethylthiophene, vinyl sulfide, 1-decanol sulfate, methyl sulfate, methyl sulfite, dichlorophenylphosphine sulfide, ethyl methyl sulfide, tetradecyl sulfate, thionaphthalene, thioaphthenequinone, 2-methylthiophene, 3-methylthiophene, a-toluenethiol, sulfur dissolved in dialkyl alkanolamine or combinations thereof.

The dehydrocylization catalyst may be any catalyst known to those of skill in the art for such purpose. For example, the dehydrocyclization catalyst can be an oxide of a Group IV-B, Group V-B or Group VI-B element. Suitable dehydrocyclization catalysts include, but are not limited to, oxides of chromium, molybdenum, tungsten, vanadium, titanium, zirconium, thioium, cerium, cesium, antimony, tin, zinc, iron, selenium, copper, platinum, palladium, nickel, cobalt or combinations thereof.

The reaction can be carried out at a temperature from about 300° C. to about 650° C., for example from about 450° C. to about 600° C. The reaction pressure can be from atmospheric to about 50 psi.

In another embodiment, the dehydrocyclization is carried out by passing the Diels-Alder cycloadduct over a steam-stable Group II metal aluminate impregnated with a Group VIII metal (U.S. Pat. No. 3,766,291). For example, the dehydrocyclization catalyst can be zinc aluminate, tin and platinum. For example, 0.4-0.6 wt % Pt on zinc aluminate, modified to contain 1 wt % tin.

In certain embodiments, the Diels-Alder reaction and the dehydrocyclization are carried out in the same reaction vessel. After completion of the Diels-Alder reaction, the catalyst for the dehydrocyclization can be added.

The reaction can be carried out at a temperature from about 750° F. to about 1250° F. or from about 900° F. to about 1050° F. The reaction pressures can be from atmospheric to about 500 psi, for example from about 50 to about 300 psi.

In yet another embodiment, the dehydrocyclization is carried out by passing the Diels-Alder cycloadduct over a catalyst consisting essentially of alumina promoted with an alkali metal oxide, and, optionally, chromium oxide (U.S. Pat. No. 4,151,071). In one embodiment, the catalyst consists essentially of alumina promoted with an oxide of sodium or potassium, rubidium or cesium, and, optionally, chromium oxide.

The reaction can be carried out at a temperature in the range of about 700° F. to about 1100° F., such as from about 800° F. to about 1050° F. The reaction pressures can be from atmospheric to about 300 psi, such as from atmospheric to about 50 psi.

The resultant bio-xylene (ortho- or para-isomer) can be purified by any method known to one of skill in the art including, but not limited to, filtration, extraction, chromatography, crystallization or membrane separation.

Isomerization of Bio-o-Xylene to Bio-p-Xylene

In some embodiments, the bio-p-xylene produced by dehydrocyclization of bio-3,6-dimethylcyclohex-1-ene is used directly for production of bio-terephthalic acid (discussed below). The bio-o-xylene produced by dehydrocyclization of bio-4,5-diemethylcyclohex-1-ene, however, should be isomerized to the bio-p-xylene isomer prior to bio-terephthalic acid formation according to the following scheme:

Scheme 9.

ortho-xylene    para-xylene

In one embodiment, the bio-o-xylene is passed over an isomerization catalyst capable of isomerizing o-xylene to p-xylene, such as a zeolite catalyst. Zeolite catalysts include, but are not limited to, acid zeolites of the type ZSM-5, ZSM-12, ZSM-35 or ZSM-38 (U.S. Pat. No. 3,856,871). In one embodiment, bio-o-xylene is vaporized and passed over a bed containing the isomerization catalyst. In another embodiment, the reaction can be conducted in the liquid phase, with sufficient pressure to retain liquidity of the bio-o-xylene. In another embodiment, the reaction can be conducted in the gaseous phase.

The reaction can be carried out at a temperature from about 300° C. to about 1000° C., such as from about 500° C. to about 800° C. or about 500° C. to about 650° C. The reaction pressure can be from about 150 psi to about 700 psi, such as from about 160 psi to about 520 psi.

In another embodiment, the zeolite catalyst also contains a metal having hydrogenation capability, such as the metals of Group VIII (U.S. Pat. No. RE31,919). In still another embodiment, the zeolite catalyst can be impregnated with a metal selected from nickel, platinum or a combination thereof.

The reaction can be carried out at a temperature from about 500° C. to about 1000° C., such as from about 600° C. to about 800° C. The reaction pressures can be from about 150 psi to about 500 psi, such as from about 150 psi to about 300 psi.

The bio-p-xylene can be purified by methods known to those skilled in the art including, but not limited to, filtration, extraction, chromatography, crystallization or membrane separation.

Oxidation of Bio-p-Xylene to Bio-Terephthalic Acid

In some embodiments of the present invention, bio-p-xylene can be oxidized to bio-terephthalic acid according to the scheme below:

Scheme 10.

para-xylene    terephthalic acid

Methods of oxidizing p-xylene to terephthalic acid are known in the art. In one embodiment, bio-p-xylene can be dissolved in a carboxylic acid-containing solvent and contacted with a catalyst. Suitable carboxylic acid-containing solvents include, but are not limited to, acetic acid, propionic acid, butyric acid, acetic anhydride or combinations thereof. In one embodiment, the solvent is acetic acid.

The catalyst can be any cobalt catalyst, as described in U.S. Pat. No. 3,334,135, such as the cobalt catalyst is $Co(OAc)_2 \cdot 4H_2O$. Manganese acetate can be used as a co-catalyst. The reaction can be carried out at a temperature from about 30° C. to about 200° C., such as from about 120° C. to about 200° C. Oxygen can be passed over the reaction mixture to effect oxidation.

In another embodiment, bromine-containing compounds can be added to the reaction mixture to accelerate the oxidation (U.S. Pat. No. 3,139,452). In one embodiment, HBr can be used in an amount corresponding to the molar equivalent of the cobalt-containing catalyst.

Bio-terephthalic acid can be esterified by conventional methods to provide the dimethyl ester, bio-dimethyl terephthalate.

The bio-terephthalic acid or bio-dimethyl terephthalate can be purified by methods known to those skilled in the art including, but not limited to, filtration, extraction, chromatography, crystallization or membrane separation.

Synthesis of Bio-PET Polymer

The bio-terephthalic acid of the present invention can be used to form a bio-PET polymer according to the following scheme:

Scheme 11.

PET

Methods of forming PET from terephthalic acid and ethylene glycol are known in the art. Any known conditions can be used for the condensation of bio-terephthalic acid (or bio-dimethyl terephthalate) and ethylene glycol.

The ethylene glycol can be derived from petrochemical-sources or biomass derived sources. Methods of preparing biomass-derived ethylene glycol (i.e. bio-ethylene glycol) are provided in WO2010/101698. In one embodiment, bio-terephthalic acid (or bio-dimethyl terephthalate) made according to the methods provided herein is condensed with petroleum-derived ethylene glycol, resulting in a bio-PET polymer that is partially derived from biomass starting materials In another embodiment, bio-terephthalic acid (or bio-dimethyl terephthalate) made according to the methods provided herein is reacted with bio-ethylene glycol, resulting in a bio-PET polymer that is derived entirely from biological starting materials The reactants can be subjected to solid state polymerization to form a bio-PET resin. For example, the method described in US2005/026728 for preparing PET can be used to form bio-PET. Briefly, a slurry of bio-terephthalic acid and bio-ethylene glycol can be prepared. Separately, a titanium complex catalyst is dispersed in a polymer matrix. The matrix is added to the slurry to promote esterification and formation of a polymer melt. The melt is used to form pellets, which are subsequently solid-state polymerized to obtain bio-PET.

In another embodiment, bio-PET is made by recycling scrap PET polymer through a degradative transesterification or hydrolysis process.

The reactants can by polymerized in a catalyst solution at atmospheric pressure to form a bio-PET polymer. Acidic or basic catalyst can be used. Suitable catalysts include, but are not limited to, antimony-containing catalysts, germanium-containing catalysts, titanium-containing catalyst and cobalt-containing catalysts. Exemplary antimony-containing catalysts include, but are not limited to, antimony trioxide, antimony triacetate or combinations thereof. Exemplary germanium-containing catalysts include, but are not limited to, germanium dioxide. Exemplary titanium-containing catalysts include, but are not limited to, tetra-n-propyltitanate, tetra-isopropyl titanate, tetra-n-butyl titanate, tetraphenyl titanate, tetracyclohexyl titanate, tetrabenzyl titanate, tetra-n-butyl titanate tetramer, titanium acetate, titanium oxalates, sodium or potassium titanates, titanium halides, titanate hexafluorides of potassium, manganese and ammonium, titanium acetylacetate, titanium alkoxides, titanate phosphites, or combinations thereof. Mixtures of various metal-containing catalysts can also be utilized.

The condensation reaction can also be induced using a coupling agent. Suitable coupling agents include, but are not limited to, carbodiimide coupling agents, for example N,N'-dicyclohexylcarbodiimide (DCC), N,N'-diisopropylcarbodiimide (DIC) or 1-Ethyl-3-(3-dimethylaminopropyl)carbodiimide hydrochloride (EDCI). Additives to promote efficient coupling can also be included, such as 1-hydroxy-1,2,3-benzotriazole (HOBt), HOBt/CuCl$_2$, 7-aza-1-hydroxy-1,2,3-benzotriazole (HOAt), 3,4-dihydro-3-hydroxy-4-oxo-1,2,3-benzotriazole (HOOBt), N-hydroxysuccinimide (NHS) or 3-sulfo-1-hydroxysuccinimide (S—NHS).

The reaction can be carried out a temperature from about 100° C. to about 500° C. For example, the reaction of bio-terephthalic acid and ethylene glycol can be carried out at a temperature from about 220° C. to about 260° C. In another example, the reaction of bio-dimethyl terephthalate and ethylene glycol can be carried out at a temperature from about 150° C. to about 280° C.

Packaging

The bio-PET polymer formed according to the method of the present invention can be used to form a bio-PET resin, which can then be formed into bio-PET performs or bio-PET packaging. The term packaging, as used herein, refers to any component of an article of packaging, including closures, labels and secondary packaging. In one embodiment, the bio-PET packaging is a food or beverage container or product, or any closure (e.g., cap), label or secondary packaging associated with the same. Food containers include, but are not limited to, disposable Tupperware, reusable Tupperware, and containers for commercial food products. Beverage containers include, but are not limited to, bottles and cups. Food products include, but are not limited to, straws, toothpicks, disposable plates and disposable cutlery.

EXAMPLES

Example 1: Diels-Alder Cycloaddition of hexa-2,4-diene and ethylene

Figure 1:
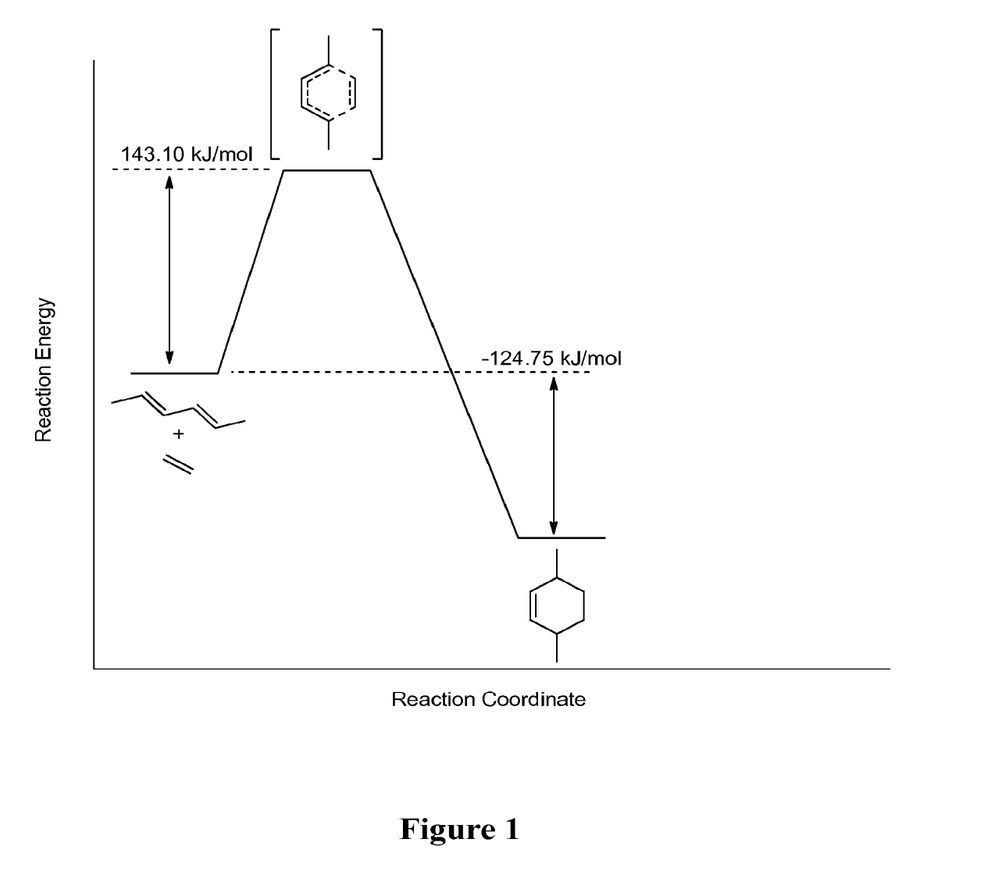
FIG. 1 shows the reaction coordinate of the Diels-Alder cycloaddition of hexa-2,4-diene and ethylene to give 3,6-dimethylcyclohex-1-ene.

The reaction coordinate of the Diels-Alder cycloaddition of hexa-2,4-diene and ethylene to give 3,6-dimethylcyclohex-1-ene is shown in FIG. 1. Computationally calculated temperature, activity ratios and reaction rates of the Diels-Alder cycloaddition are shown in Table 1, and are based on the Eyering equation:

$$k=(k_B t/h)^{(-Ea/RT)}$$

where k=rate constant;
$K_B$=Boltzmann constant;
T=temperature;
h=Plank's constant; and
Ea=Activation energy (143.1 kJ/mol)

The "Ratio" is defined as the moles of ethylene to moles of hexa-2,4-diene.

TABLE 1

| Temperature | | | Ratio | | | | | | |
|---|---|---|---|---|---|---|---|---|---|
| K | ° C. | k (1/s) | 1 | 2 | 5 | 10 | 25 | 50 | 100 |
| 298.15 | 25 | 5.27E−16 | 5.27E−16 | 1.05E−15 | 2.64E−15 | 5.27E−15 | 1.32E−14 | 2.64E−14 | 5.27E−14 |
| 303.15 | 30 | 1.39E−15 | 1.39E−15 | 2.78E−15 | 6.94E−15 | 1.39E−14 | 3.47E−14 | 6.94E−14 | 1.39E−13 |
| 308.15 | 35 | 3.55E−15 | 3.55E−15 | 7.09E−15 | 1.77E−14 | 3.55E−14 | 8.87E−14 | 1.77E−13 | 3.55E−13 |
| 313.15 | 40 | 8.79E−15 | 8.79E−15 | 1.76E−14 | 4.40E−14 | 8.79E−14 | 2.20E−13 | 4.40E−13 | 8.79E−13 |
| 318.15 | 45 | 2.12E−14 | 2.12E−14 | 4.24E−14 | 1.06E−13 | 2.12E−13 | 5.30E−13 | 1.06E−12 | 2.12E−12 |
| 323.15 | 50 | 4.97E−14 | 4.97E−14 | 9.94E−14 | 2.49E−13 | 4.97E−13 | 1.24E−12 | 2.49E−12 | 4.97E−12 |
| 328.15 | 55 | 1.14E−13 | 1.14E−13 | 2.27E−13 | 5.68E−13 | 1.14E−12 | 2.84E−12 | 5.68E−12 | 1.14E−11 |
| 333.15 | 60 | 2.53E−13 | 2.53E−13 | 5.07E−13 | 1.27E−12 | 2.53E−12 | 6.34E−12 | 1.27E−11 | 2.53E−11 |
| 338.15 | 65 | 5.52E−13 | 5.52E−13 | 1.10E−12 | 2.76E−12 | 5.52E−12 | 1.38E−11 | 2.76E−11 | 5.52E−11 |
| 343.15 | 70 | 1.18E−12 | 1.18E−12 | 2.35E−12 | 5.88E−12 | 1.18E−11 | 2.94E−11 | 5.88E−11 | 1.18E−10 |
| 348.15 | 75 | 2.45E−12 | 2.45E−12 | 4.91E−12 | 1.23E−11 | 2.45E−11 | 6.13E−11 | 1.23E−10 | 2.45E−10 |
| 353.15 | 80 | 5.01E−12 | 5.01E−12 | 1.00E−11 | 2.51E−11 | 5.01E−11 | 1.25E−10 | 2.51E−10 | 5.01E−10 |
| 358.15 | 85 | 1.00E−11 | 1.00E−11 | 2.01E−11 | 5.02E−11 | 1.00E−10 | 2.51E−10 | 5.02E−10 | 1.00E−09 |
| 363.15 | 90 | 1.97E−11 | 1.97E−11 | 3.94E−11 | 9.86E−11 | 1.97E−10 | 4.93E−10 | 9.86E−10 | 1.97E−09 |
| 368.15 | 95 | 3.81E−11 | 3.81E−11 | 7.61E−11 | 1.90E−10 | 3.81E−10 | 9.52E−10 | 1.90E−09 | 3.81E−09 |
| 373.15 | 100 | 7.22E−11 | 7.22E−11 | 1.44E−10 | 3.61E−10 | 7.22E−10 | 1.80E−09 | 3.61E−09 | 7.22E−09 |
| 378.15 | 105 | 1.35E−10 | 1.35E−10 | 2.69E−10 | 6.73E−10 | 1.35E−09 | 3.37E−09 | 6.73E−09 | 1.35E−08 |
| 383.15 | 110 | 2.47E−10 | 2.47E−10 | 4.94E−10 | 1.24E−09 | 2.47E−09 | 6.18E−09 | 1.24E−08 | 2.47E−08 |
| 388.15 | 115 | 4.46E−10 | 4.46E−10 | 8.93E−10 | 2.23E−09 | 4.46E−09 | 1.12E−08 | 2.23E−08 | 4.46E−08 |

TABLE 1-continued

| Temperature | | | Ratio | | | | | | |
|---|---|---|---|---|---|---|---|---|---|
| K | °C. | k (1/s) | 1 | 2 | 5 | 10 | 25 | 50 | 100 |
| 393.15 | 120 | 7.95E−10 | 7.95E−10 | 1.59E−09 | 3.97E−09 | 7.95E−09 | 1.99E−08 | 3.97E−08 | 7.95E−08 |
| 398.15 | 125 | 1.39E−09 | 1.39E−09 | 2.79E−09 | 6.97E−09 | 1.39E−08 | 3.49E−08 | 6.97E−08 | 1.39E−07 |
| 403.15 | 130 | 2.41E−09 | 2.41E−09 | 4.83E−09 | 1.21E−08 | 2.41E−08 | 6.03E−08 | 1.21E−07 | 2.41E−07 |
| 408.15 | 135 | 4.12E−09 | 4.12E−09 | 8.25E−09 | 2.06E−08 | 4.12E−08 | 1.03E−07 | 2.06E−07 | 4.12E−07 |
| 413.15 | 140 | 6.95E−09 | 6.95E−09 | 1.39E−08 | 3.48E−08 | 6.95E−08 | 1.74E−07 | 3.48E−07 | 6.95E−07 |
| 418.15 | 145 | 1.16E−08 | 1.16E−08 | 2.32E−08 | 5.79E−08 | 1.16E−07 | 2.89E−07 | 5.79E−07 | 1.16E−06 |
| 423.15 | 150 | 1.91E−08 | 1.91E−08 | 3.81E−08 | 9.53E−08 | 1.91E−07 | 4.76E−07 | 9.53E−07 | 1.91E−06 |
| 428.15 | 155 | 3.10E−08 | 3.10E−08 | 6.20E−08 | 1.55E−07 | 3.10E−07 | 7.75E−07 | 1.55E−06 | 3.10E−06 |
| 433.15 | 160 | 4.99E−08 | 4.99E−08 | 9.98E−08 | 2.49E−07 | 4.99E−07 | 1.25E−06 | 2.49E−06 | 4.99E−06 |
| 438.15 | 165 | 7.94E−08 | 7.94E−08 | 1.59E−07 | 3.97E−07 | 7.94E−07 | 1.99E−06 | 3.97E−06 | 7.94E−06 |
| 443.15 | 170 | 1.25E−07 | 1.25E−07 | 2.50E−07 | 6.26E−07 | 1.25E−06 | 3.13E−06 | 6.26E−06 | 1.25E−05 |
| 448.15 | 175 | 1.95E−07 | 1.95E−07 | 3.90E−07 | 9.76E−07 | 1.95E−06 | 4.88E−06 | 9.76E−06 | 1.95E−05 |
| 453.15 | 180 | 3.02E−07 | 3.02E−07 | 6.03E−07 | 1.51E−06 | 3.02E−06 | 7.54E−06 | 1.51E−05 | 3.02E−05 |
| 458.15 | 185 | 4.61E−07 | 4.61E−07 | 9.23E−07 | 2.31E−06 | 4.61E−06 | 1.15E−05 | 2.31E−05 | 4.61E−05 |
| 463.15 | 190 | 7.00E−07 | 7.00E−07 | 1.40E−06 | 3.50E−06 | 7.00E−06 | 1.75E−05 | 3.50E−05 | 7.00E−05 |
| 468.15 | 195 | 1.05E−06 | 1.05E−06 | 2.10E−06 | 5.26E−06 | 1.05E−05 | 2.63E−05 | 5.26E−05 | 1.05E−04 |
| 473.15 | 200 | 1.57E−06 | 1.57E−06 | 3.14E−06 | 7.84E−06 | 1.57E−05 | 3.92E−05 | 7.84E−05 | 1.57E−04 |
| 478.15 | 205 | 2.32E−06 | 2.32E−06 | 4.64E−06 | 1.16E−05 | 2.32E−05 | 5.79E−05 | 1.16E−04 | 2.32E−04 |
| 483.15 | 210 | 3.40E−06 | 3.40E−06 | 6.80E−06 | 1.70E−05 | 3.40E−05 | 8.50E−05 | 1.70E−04 | 3.40E−04 |
| 488.15 | 215 | 4.95E−06 | 4.95E−06 | 9.89E−06 | 2.47E−05 | 4.95E−05 | 1.24E−04 | 2.47E−04 | 4.95E−04 |
| 493.15 | 220 | 7.15E−06 | 7.15E−06 | 1.43E−05 | 3.57E−05 | 7.15E−05 | 1.79E−04 | 3.57E−04 | 7.15E−04 |
| 498.15 | 225 | 1.02E−05 | 1.02E−05 | 2.05E−05 | 5.12E−05 | 1.02E−04 | 2.56E−04 | 5.12E−04 | 1.02E−03 |
| 503.15 | 230 | 1.46E−05 | 1.46E−05 | 2.92E−05 | 7.29E−05 | 1.46E−04 | 3.65E−04 | 7.29E−04 | 1.46E−03 |
| 508.15 | 235 | 2.06E−05 | 2.06E−05 | 4.13E−05 | 1.03E−04 | 2.06E−04 | 5.16E−04 | 1.03E−03 | 2.06E−03 |
| 513.15 | 240 | 2.90E−05 | 2.90E−05 | 5.80E−05 | 1.45E−04 | 2.90E−04 | 7.24E−04 | 1.45E−03 | 2.90E−03 |
| 518.15 | 245 | 4.04E−05 | 4.04E−05 | 8.09E−05 | 2.02E−04 | 4.04E−04 | 1.01E−03 | 2.02E−03 | 4.04E−03 |
| 523.15 | 250 | 5.61E−05 | 5.61E−05 | 1.12E−04 | 2.80E−04 | 5.61E−04 | 1.40E−03 | 2.80E−03 | 5.61E−03 |
| 528.15 | 255 | 7.73E−05 | 7.73E−05 | 1.55E−04 | 3.87E−04 | 7.73E−04 | 1.93E−03 | 3.87E−03 | 7.73E−03 |
| 533.15 | 260 | 1.06E−04 | 1.06E−04 | 2.12E−04 | 5.30E−04 | 1.06E−03 | 2.65E−03 | 5.30E−03 | 1.06E−02 |
| 538.15 | 265 | 1.44E−04 | 1.44E−04 | 2.89E−04 | 7.22E−04 | 1.44E−03 | 3.61E−03 | 7.22E−03 | 1.44E−02 |
| 543.15 | 270 | 1.96E−04 | 1.96E−04 | 3.91E−04 | 9.78E−04 | 1.96E−03 | 4.89E−03 | 9.78E−03 | 1.96E−02 |
| 548.15 | 275 | 2.64E−04 | 2.64E−04 | 5.27E−04 | 1.32E−03 | 2.64E−03 | 6.59E−03 | 1.32E−02 | 2.64E−02 |
| 553.15 | 280 | 3.53E−04 | 3.53E−04 | 7.06E−04 | 1.77E−03 | 3.53E−03 | 8.83E−03 | 1.77E−02 | 3.53E−02 |
| 558.15 | 285 | 4.71E−04 | 4.71E−04 | 9.42E−04 | 2.35E−03 | 4.71E−03 | 1.18E−02 | 2.35E−02 | 4.71E−02 |
| 563.15 | 290 | 6.25E−04 | 6.25E−04 | 1.25E−03 | 3.12E−03 | 6.25E−03 | 1.56E−02 | 3.12E−02 | 6.25E−02 |
| 568.15 | 295 | 8.25E−04 | 8.25E−04 | 1.65E−03 | 4.12E−03 | 8.25E−03 | 2.06E−02 | 4.12E−02 | 8.25E−02 |
| 573.15 | 300 | 1.08E−03 | 1.08E−03 | 2.17E−03 | 5.42E−03 | 1.08E−02 | 2.71E−02 | 5.42E−02 | 1.08E−01 |
| 578.15 | 305 | 1.42E−03 | 1.42E−03 | 2.84E−03 | 7.09E−03 | 1.42E−02 | 3.54E−02 | 7.09E−02 | 1.42E−01 |
| 583.15 | 310 | 1.85E−03 | 1.85E−03 | 3.69E−03 | 9.23E−03 | 1.85E−02 | 4.61E−02 | 9.23E−02 | 1.85E−01 |
| 588.15 | 315 | 2.39E−03 | 2.39E−03 | 4.79E−03 | 1.20E−02 | 2.39E−02 | 5.98E−02 | 1.20E−01 | 2.39E−01 |
| 593.15 | 320 | 3.09E−03 | 3.09E−03 | 6.18E−03 | 1.54E−02 | 3.09E−02 | 7.72E−02 | 1.54E−01 | 3.09E−01 |
| 598.15 | 325 | 3.97E−03 | 3.97E−03 | 7.94E−03 | 1.98E−02 | 3.97E−02 | 9.92E−02 | 1.98E−01 | 3.97E−01 |
| 603.15 | 330 | 5.08E−03 | 5.08E−03 | 1.02E−02 | 2.54E−02 | 5.08E−02 | 1.27E−01 | 2.54E−01 | 5.08E−01 |
| 608.15 | 335 | 6.48E−03 | 6.48E−03 | 1.30E−02 | 3.24E−02 | 6.48E−02 | 1.62E−01 | 3.24E−01 | 6.48E−01 |
| 613.15 | 340 | 8.23E−03 | 8.23E−03 | 1.65E−02 | 4.11E−02 | 8.23E−02 | 2.06E−01 | 4.11E−01 | 8.23E−01 |
| 618.15 | 345 | 1.04E−02 | 1.04E−02 | 2.08E−02 | 5.20E−02 | 1.04E−01 | 2.60E−01 | 5.20E−01 | 1.04E+00 |
| 623.15 | 350 | 1.31E−02 | 1.31E−02 | 2.62E−02 | 6.56E−02 | 1.31E−01 | 3.28E−01 | 6.56E−01 | 1.31E+00 |
| 628.15 | 355 | 1.65E−02 | 1.65E−02 | 3.29E−02 | 8.24E−02 | 1.65E−01 | 4.12E−01 | 8.24E−01 | 1.65E+00 |
| 633.15 | 360 | 2.06E−02 | 2.06E−02 | 4.12E−02 | 1.03E−01 | 2.06E−01 | 5.15E−01 | 1.03E+00 | 2.06E+00 |
| 638.15 | 365 | 2.57E−02 | 2.57E−02 | 5.14E−02 | 1.29E−01 | 2.57E−01 | 6.43E−01 | 1.29E+00 | 2.57E+00 |
| 643.15 | 370 | 3.20E−02 | 3.20E−02 | 6.39E−02 | 1.60E−01 | 3.20E−01 | 7.99E−01 | 1.60E+00 | 3.20E+00 |
| 648.15 | 375 | 3.96E−02 | 3.96E−02 | 7.92E−02 | 1.98E−01 | 3.96E−01 | 9.90E−01 | 1.98E+00 | 3.96E+00 |
| 653.15 | 380 | 4.89E−02 | 4.89E−02 | 9.78E−02 | 2.44E−01 | 4.89E−01 | 1.22E+00 | 2.44E+00 | 4.89E+00 |
| 658.15 | 385 | 6.02E−02 | 6.02E−02 | 1.20E−01 | 3.01E−01 | 6.02E−01 | 1.50E+00 | 3.01E+00 | 6.02E+00 |
| 663.15 | 390 | 7.39E−02 | 7.39E−02 | 1.48E−01 | 3.69E−01 | 7.39E−01 | 1.85E+00 | 3.69E+00 | 7.39E+00 |
| 668.15 | 395 | 9.04E−02 | 9.04E−02 | 1.81E−01 | 4.52E−01 | 9.04E−01 | 2.26E+00 | 4.52E+00 | 9.04E+00 |
| 673.15 | 400 | 1.10E−01 | 1.10E−01 | 2.20E−01 | 5.51E−01 | 1.10E+00 | 2.76E+00 | 5.51E+00 | 1.10E+01 |
| 678.15 | 405 | 1.34E−01 | 1.34E−01 | 2.68E−01 | 6.71E−01 | 1.34E+00 | 3.35E+00 | 6.71E+00 | 1.34E+01 |
| 683.15 | 410 | 1.63E−01 | 1.63E−01 | 3.25E−01 | 8.13E−01 | 1.63E+00 | 4.07E+00 | 8.13E+00 | 1.63E+01 |
| 688.15 | 415 | 1.97E−01 | 1.97E−01 | 3.94E−01 | 9.84E−01 | 1.97E+00 | 4.92E+00 | 9.84E+00 | 1.97E+01 |
| 693.15 | 420 | 2.37E−01 | 2.37E−01 | 4.75E−01 | 1.19E+00 | 2.37E+00 | 5.93E+00 | 1.19E+01 | 2.37E+01 |
| 698.15 | 425 | 2.86E−01 | 2.86E−01 | 5.71E−01 | 1.43E+00 | 2.86E+00 | 7.14E+00 | 1.43E+01 | 2.86E+01 |

Example 2: Diels-Alder Cycloaddition of hexa-2,4-diene and ethylene

Figure 2:
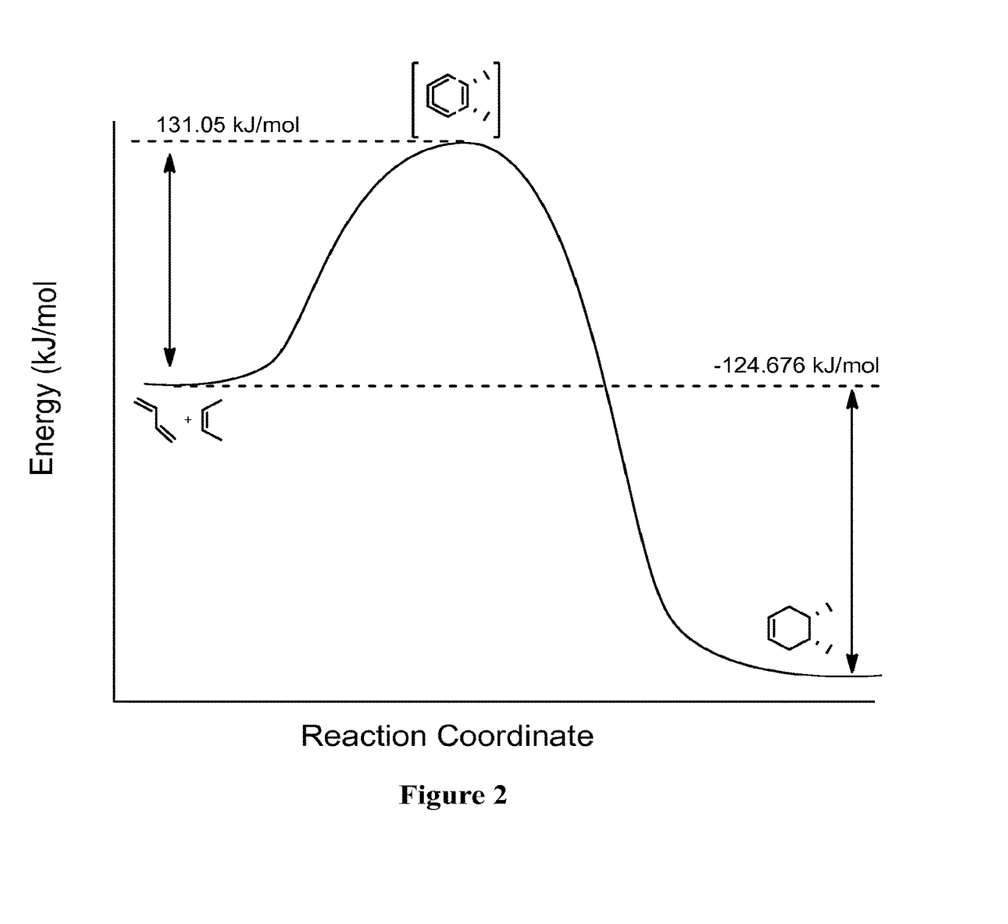
FIG. 2 shows the reaction coordinate of the Diels-Alder cycloaddition of buta-1,3-diene and 2-butene to produce 4,5-dimethylcyclohex-1-ene.

The reaction coordinate of the Diels-Alder cycloaddition of buta-1,3-diene and 2-butene to produce the [4+2] cycloadduct, 4,5-dimethylcyclohex-1-ene is shown in FIG. 2. Computationally calculated temperature, activity ratios and reaction rates of the Diels-Alder cycloaddition are shown in Table 2, and are based on the Eyering equation:

$$k = (k_B t/h)^{(-E_a/RT)}$$

where k=rate constant;
$K_B$=Boltzmann constant;
h=Plank's constant;
T=temperature; and
Ea=Activation energy (131.05 kJ/mol)

The "Ratio" is defined as the molar concentration of 2-butene to the molar concentration of buta-1,3-diene.

TABLE 2

| Temperature | | | Ratio | | | | | | |
|---|---|---|---|---|---|---|---|---|---|
| K | °C. | k (1/s) | 1 | 2 | 5 | 10 | 25 | 50 | 100 |
| 298.15 | 25 | 6.81E−14 | 6.81E−14 | 1.36E−13 | 3.40E−13 | 6.81E−13 | 1.70E−12 | 3.40E−12 | 6.81E−12 |
| 303.15 | 30 | 1.66E−13 | 1.66E−13 | 3.31E−13 | 8.28E−13 | 1.66E−12 | 4.14E−12 | 8.28E−12 | 1.66E−11 |
| 308.15 | 35 | 3.91E−13 | 3.91E−13 | 7.82E−13 | 1.96E−12 | 3.91E−12 | 9.78E−12 | 1.96E−11 | 3.91E−11 |
| 313.15 | 40 | 9.00E−13 | 9.00E−13 | 1.80E−12 | 4.50E−12 | 9.00E−12 | 2.25E−11 | 4.50E−11 | 9.00E−11 |
| 318.15 | 45 | 2.02E−12 | 2.02E−12 | 4.03E−12 | 1.01E−11 | 2.02E−11 | 5.04E−11 | 1.01E−10 | 2.02E−10 |
| 323.15 | 50 | 4.41E−12 | 4.41E−12 | 8.82E−12 | 2.20E−11 | 4.41E−11 | 1.10E−10 | 2.20E−10 | 4.41E−10 |
| 328.15 | 55 | 9.41E−12 | 9.41E−12 | 1.88E−11 | 4.71E−11 | 9.41E−11 | 2.35E−10 | 4.71E−10 | 9.41E−10 |
| 333.15 | 60 | 1.96E−11 | 1.96E−11 | 3.93E−11 | 9.82E−11 | 1.96E−10 | 4.91E−10 | 9.82E−10 | 1.96E−09 |
| 338.15 | 65 | 4.01E−11 | 4.01E−11 | 8.03E−11 | 2.01E−10 | 4.01E−10 | 1.00E−09 | 2.01E−09 | 4.01E−09 |
| 343.15 | 70 | 8.04E−11 | 8.04E−11 | 1.61E−10 | 4.02E−10 | 8.04E−10 | 2.01E−09 | 4.02E−09 | 8.04E−09 |
| 348.15 | 75 | 1.58E−10 | 1.58E−10 | 3.15E−10 | 7.88E−10 | 1.58E−09 | 3.94E−09 | 7.88E−09 | 1.58E−08 |
| 353.15 | 80 | 3.04E−10 | 3.04E−10 | 6.07E−10 | 1.52E−09 | 3.04E−09 | 7.59E−09 | 1.52E−08 | 3.04E−08 |
| 358.15 | 85 | 5.74E−10 | 5.74E−10 | 1.15E−09 | 2.87E−09 | 5.74E−09 | 1.44E−08 | 2.87E−08 | 5.74E−08 |
| 363.15 | 90 | 1.07E−09 | 1.07E−09 | 2.13E−09 | 5.34E−09 | 1.07E−08 | 2.67E−08 | 5.34E−08 | 1.07E−07 |
| 368.15 | 95 | 1.95E−09 | 1.95E−09 | 3.90E−09 | 9.75E−09 | 1.95E−08 | 4.88E−08 | 9.75E−08 | 1.95E−07 |
| 373.15 | 100 | 3.51E−09 | 3.51E−09 | 7.02E−09 | 1.75E−08 | 3.51E−08 | 8.77E−08 | 1.75E−07 | 3.51E−07 |
| 378.15 | 105 | 6.22E−09 | 6.22E−09 | 1.24E−08 | 3.11E−08 | 6.22E−08 | 1.55E−07 | 3.11E−07 | 6.22E−07 |
| 383.15 | 110 | 1.09E−08 | 1.09E−08 | 2.17E−08 | 5.43E−08 | 1.09E−07 | 2.71E−07 | 5.43E−07 | 1.09E−06 |
| 388.15 | 115 | 1.87E−08 | 1.87E−08 | 3.74E−08 | 9.34E−08 | 1.87E−07 | 4.67E−07 | 9.34E−07 | 1.87E−06 |
| 393.15 | 120 | 3.17E−08 | 3.17E−08 | 6.34E−08 | 1.59E−07 | 3.17E−07 | 7.93E−07 | 1.59E−06 | 3.17E−06 |
| 398.15 | 125 | 5.31E−08 | 5.31E−08 | 1.06E−07 | 2.66E−07 | 5.31E−07 | 1.33E−06 | 2.66E−06 | 5.31E−06 |
| 403.15 | 130 | 8.79E−08 | 8.79E−08 | 1.76E−07 | 4.40E−07 | 8.79E−07 | 2.20E−06 | 4.40E−06 | 8.79E−06 |
| 408.15 | 135 | 1.44E−07 | 1.44E−07 | 2.87E−07 | 7.18E−07 | 1.44E−06 | 3.59E−06 | 7.18E−06 | 1.44E−05 |
| 413.15 | 140 | 2.32E−07 | 2.32E−07 | 4.64E−07 | 1.16E−06 | 2.32E−06 | 5.80E−06 | 1.16E−05 | 2.32E−05 |
| 418.15 | 145 | 3.71E−07 | 3.71E−07 | 7.41E−07 | 1.85E−06 | 3.71E−06 | 9.27E−06 | 1.85E−05 | 3.71E−05 |
| 423.15 | 150 | 5.86E−07 | 5.86E−07 | 1.17E−06 | 2.93E−06 | 5.86E−06 | 1.46E−05 | 2.93E−05 | 5.86E−05 |
| 428.15 | 155 | 9.15E−07 | 9.15E−07 | 1.83E−06 | 4.58E−06 | 9.15E−06 | 2.29E−05 | 4.58E−05 | 9.15E−05 |
| 433.15 | 160 | 1.42E−06 | 1.42E−06 | 2.83E−06 | 7.08E−06 | 1.42E−05 | 3.54E−05 | 7.08E−05 | 1.42E−04 |
| 438.15 | 165 | 2.17E−06 | 2.17E−06 | 4.34E−06 | 1.09E−05 | 2.17E−05 | 5.43E−05 | 1.09E−04 | 2.17E−04 |
| 443.15 | 170 | 3.29E−06 | 3.29E−06 | 6.59E−06 | 1.65E−05 | 3.29E−05 | 8.24E−05 | 1.65E−04 | 3.29E−04 |
| 448.15 | 175 | 4.95E−06 | 4.95E−06 | 9.91E−06 | 2.48E−05 | 4.95E−05 | 1.24E−04 | 2.48E−04 | 4.95E−04 |
| 453.15 | 180 | 7.39E−06 | 7.39E−06 | 1.48E−05 | 3.69E−05 | 7.39E−05 | 1.85E−04 | 3.69E−04 | 7.39E−04 |
| 458.15 | 185 | 1.09E−05 | 1.09E−05 | 2.18E−05 | 5.46E−05 | 1.09E−04 | 2.73E−04 | 5.46E−04 | 1.09E−03 |
| 463.15 | 190 | 1.60E−05 | 1.60E−05 | 3.20E−05 | 8.00E−05 | 1.60E−04 | 4.00E−04 | 8.00E−04 | 1.60E−03 |
| 468.15 | 195 | 2.33E−05 | 2.33E−05 | 4.65E−05 | 1.16E−04 | 2.33E−04 | 5.81E−04 | 1.16E−03 | 2.33E−03 |
| 473.15 | 200 | 3.35E−05 | 3.35E−05 | 6.71E−05 | 1.68E−04 | 3.35E−04 | 8.39E−04 | 1.68E−03 | 3.35E−03 |
| 478.15 | 205 | 4.80E−05 | 4.80E−05 | 9.61E−05 | 2.40E−04 | 4.80E−04 | 1.20E−03 | 2.40E−03 | 4.80E−03 |
| 483.15 | 210 | 6.83E−05 | 6.83E−05 | 1.37E−04 | 3.41E−04 | 6.83E−04 | 1.71E−03 | 3.41E−03 | 6.83E−03 |
| 488.15 | 215 | 9.63E−05 | 9.63E−05 | 1.93E−04 | 4.82E−04 | 9.63E−04 | 2.41E−03 | 4.82E−03 | 9.63E−03 |
| 493.15 | 220 | 1.35E−04 | 1.35E−04 | 2.70E−04 | 6.75E−04 | 1.35E−03 | 3.38E−03 | 6.75E−03 | 1.35E−02 |
| 498.15 | 225 | 1.88E−04 | 1.88E−04 | 3.76E−04 | 9.40E−04 | 1.88E−03 | 4.70E−03 | 9.40E−03 | 1.88E−02 |
| 503.15 | 230 | 2.60E−04 | 2.60E−04 | 5.20E−04 | 1.30E−03 | 2.60E−03 | 6.50E−03 | 1.30E−02 | 2.60E−02 |
| 508.15 | 235 | 3.57E−04 | 3.57E−04 | 7.15E−04 | 1.79E−03 | 3.57E−03 | 8.94E−03 | 1.79E−02 | 3.57E−02 |
| 513.15 | 240 | 4.88E−04 | 4.88E−04 | 9.77E−04 | 2.44E−03 | 4.88E−03 | 1.22E−02 | 2.44E−02 | 4.88E−02 |
| 518.15 | 245 | 6.63E−04 | 6.63E−04 | 1.33E−03 | 3.32E−03 | 6.63E−03 | 1.66E−02 | 3.32E−02 | 6.63E−02 |
| 523.15 | 250 | 8.96E−04 | 8.96E−04 | 1.79E−03 | 4.48E−03 | 8.96E−03 | 2.24E−02 | 4.48E−02 | 8.96E−02 |
| 528.15 | 255 | 1.20E−03 | 1.20E−03 | 2.41E−03 | 6.01E−03 | 1.20E−02 | 3.01E−02 | 6.01E−02 | 1.20E−01 |
| 533.15 | 260 | 1.61E−03 | 1.61E−03 | 3.21E−03 | 8.03E−03 | 1.61E−02 | 4.02E−02 | 8.03E−02 | 1.61E−01 |
| 538.15 | 265 | 2.13E−03 | 2.13E−03 | 4.27E−03 | 1.07E−02 | 2.13E−02 | 5.33E−02 | 1.07E−01 | 2.13E−01 |
| 543.15 | 270 | 2.82E−03 | 2.82E−03 | 5.64E−03 | 1.41E−02 | 2.82E−02 | 7.05E−02 | 1.41E−01 | 2.82E−01 |
| 548.15 | 275 | 3.71E−03 | 3.71E−03 | 7.42E−03 | 1.85E−02 | 3.71E−02 | 9.27E−02 | 1.85E−01 | 3.71E−01 |
| 553.15 | 280 | 4.85E−03 | 4.85E−03 | 9.71E−03 | 2.43E−02 | 4.85E−02 | 1.21E−01 | 2.43E−01 | 4.85E−01 |
| 558.15 | 285 | 6.32E−03 | 6.32E−03 | 1.26E−02 | 3.16E−02 | 6.32E−02 | 1.58E−01 | 3.16E−01 | 6.32E−01 |
| 563.15 | 290 | 8.19E−03 | 8.19E−03 | 1.64E−02 | 4.10E−02 | 8.19E−02 | 2.05E−01 | 4.10E−01 | 8.19E−01 |
| 568.15 | 295 | 1.06E−02 | 1.06E−02 | 2.12E−02 | 5.29E−02 | 1.06E−01 | 2.64E−01 | 5.29E−01 | 1.06E+00 |
| 573.15 | 300 | 1.36E−02 | 1.36E−02 | 2.72E−02 | 6.80E−02 | 1.36E−01 | 3.40E−01 | 6.80E−01 | 1.36E+00 |
| 578.15 | 305 | 1.74E−02 | 1.74E−02 | 3.48E−02 | 8.70E−02 | 1.74E−01 | 4.35E−01 | 8.70E−01 | 1.74E+00 |
| 583.15 | 310 | 2.22E−02 | 2.22E−02 | 4.43E−02 | 1.11E−01 | 2.22E−01 | 5.54E−01 | 1.11E+00 | 2.22E+00 |
| 588.15 | 315 | 2.81E−02 | 2.81E−02 | 5.63E−02 | 1.41E−01 | 2.81E−01 | 7.03E−01 | 1.41E+00 | 2.81E+00 |
| 593.15 | 320 | 3.56E−02 | 3.56E−02 | 7.11E−02 | 1.78E−01 | 3.56E−01 | 8.89E−01 | 1.78E+00 | 3.56E+00 |
| 598.15 | 325 | 4.48E−02 | 4.48E−02 | 8.95E−02 | 2.24E−01 | 4.48E−01 | 1.12E+00 | 2.24E+00 | 4.48E+00 |
| 603.15 | 330 | 5.62E−02 | 5.62E−02 | 1.12E−01 | 2.81E−01 | 5.62E−01 | 1.40E+00 | 2.81E+00 | 5.62E+00 |
| 608.15 | 335 | 7.02E−02 | 7.02E−02 | 1.40E−01 | 3.51E−01 | 7.02E−01 | 1.76E+00 | 3.51E+00 | 7.02E+00 |
| 613.15 | 340 | 8.74E−02 | 8.74E−02 | 1.75E−01 | 4.37E−01 | 8.74E−01 | 2.19E+00 | 4.37E+00 | 8.74E+00 |
| 618.15 | 345 | 1.09E−01 | 1.09E−01 | 2.17E−01 | 5.43E−01 | 1.09E+00 | 2.71E+00 | 5.43E+00 | 1.09E+01 |
| 623.15 | 350 | 1.34E−01 | 1.34E−01 | 2.69E−01 | 6.71E−01 | 1.34E+00 | 3.36E+00 | 6.71E+00 | 1.34E+01 |
| 628.15 | 355 | 1.66E−01 | 1.66E−01 | 3.31E−01 | 8.28E−01 | 1.66E+00 | 4.14E+00 | 8.28E+00 | 1.66E+01 |
| 633.15 | 360 | 2.03E−01 | 2.03E−01 | 4.07E−01 | 1.02E+00 | 2.03E+00 | 5.08E+00 | 1.02E+01 | 2.03E+01 |
| 638.15 | 365 | 2.49E−01 | 2.49E−01 | 4.98E−01 | 1.25E+00 | 2.49E+00 | 6.23E+00 | 1.25E+01 | 2.49E+01 |
| 643.15 | 370 | 3.04E−01 | 3.04E−01 | 6.09E−01 | 1.52E+00 | 3.04E+00 | 7.61E+00 | 1.52E+01 | 3.04E+01 |
| 648.15 | 375 | 3.70E−01 | 3.70E−01 | 7.41E−01 | 1.85E+00 | 3.70E+00 | 9.26E+00 | 1.85E+01 | 3.70E+01 |
| 653.15 | 380 | 4.50E−01 | 4.50E−01 | 8.99E−01 | 2.25E+00 | 4.50E+00 | 1.12E+01 | 2.25E+01 | 4.50E+01 |
| 658.15 | 385 | 5.44E−01 | 5.44E−01 | 1.09E+00 | 2.72E+00 | 5.44E+00 | 1.36E+01 | 2.72E+01 | 5.44E+01 |
| 663.15 | 390 | 6.57E−01 | 6.57E−01 | 1.31E+00 | 3.29E+00 | 6.57E+00 | 1.64E+01 | 3.29E+01 | 6.57E+01 |
| 668.15 | 395 | 7.91E−01 | 7.91E−01 | 1.58E+00 | 3.95E+00 | 7.91E+00 | 1.98E+01 | 3.95E+01 | 7.91E+01 |
| 673.15 | 400 | 9.49E−01 | 9.49E−01 | 1.90E+00 | 4.75E+00 | 9.49E+00 | 2.37E+01 | 4.75E+01 | 9.49E+01 |

TABLE 2-continued

| Temperature | | | Ratio | | | | | | |
|---|---|---|---|---|---|---|---|---|---|
| K | °C. | k (1/s) | 1 | 2 | 5 | 10 | 25 | 50 | 100 |
| 678.15 | 405 | 1.14E+00 | 1.14E+00 | 2.27E+00 | 5.68E+00 | 1.14E+01 | 2.84E+01 | 5.68E+01 | 1.14E+02 |
| 683.15 | 410 | 1.36E+00 | 1.36E+00 | 2.71E+00 | 6.79E+00 | 1.36E+01 | 3.39E+01 | 6.79E+01 | 1.36E+02 |
| 688.15 | 415 | 1.62E+00 | 1.62E+00 | 3.23E+00 | 8.08E+00 | 1.62E+01 | 4.04E+01 | 8.08E+01 | 1.62E+02 |
| 693.15 | 420 | 1.92E+00 | 1.92E+00 | 3.84E+00 | 9.61E+00 | 1.92E+01 | 4.80E+01 | 9.61E+01 | 1.92E+02 |
| 698.15 | 425 | 2.28E+00 | 2.28E+00 | 4.55E+00 | 1.14E+01 | 2.28E+01 | 5.69E+01 | 1.14E+02 | 2.28E+02 |

DISCUSSION

Tables 1 and 2 illustrate that increasing the activity ratio of diene to dienophile, regardless of temperature, increases the rate of the cycloaddition reaction. Similarly, increasing the temperature of the reaction, regardless of the activity ratio, increases the rate of the cycloaddition reaction. The fastest reaction rates occur at maximum activity ratio and maximum temperature.

What is claimed is:

1. A method of preparing bio-p-xylene comprising:
deriving bio-glucose from at least one biomass source;
converting bio-glucose to bio-ethanol;
converting a first portion of bio-ethanol to bio-ethylene,
converting a second portion of bio-ethanol to bio-hexa-2,4-diene,
reacting bio-ethylene and bio-hexa-2,4-diene under Diels-Alder cycloaddition conditions to form bio-3,6-dimethylcyclohex-1-ene, wherein the molar ratio of bio-ethylene to bio-hexa-2,4-diene is at least about 50:1, the temperature is from about 100° C. to about 700° C., the cycloaddition is carried out at atmospheric pressure and the cycloaddition proceeds for from about 5 minutes to about 24 hours and results in greater than 90% yield; and
dehydrocyclizing bio-3,6-dimethylcyclohex-1-ene to bio-p-xylene.

2. The method of claim 1, further comprising oxidation of bio-p-xylene to provide bio-terephthalic acid.

3. The method of claim 1, wherein the molar ratio of the Diels-Alder cycloaddition is at least about 100:1.

4. The method of claim 1, wherein the temperature of the Diels-Alder cycloaddition is from about 500° C. to about 700° C.

5. The method of claim 1, wherein the temperature of the Diels-Alder cycloaddition is from about 500° C. to about 700° C. and the molar ratio is from about 50:1 to about 100:1.

6. The method of claim 2, further comprising condensing the bio-terephthalic acid and ethylene glycol to provide a bio-PET polymer.

7. The method of claim 1 wherein the at least one biomass source is selected from the group consisting of corn, maize, sorghum, barley, wheat, rye, rice, millet, barley, potato, sugarcane, sugar beet, tubers, soybeans, molasses, fruit materials, sugar cane, sugar beet, wood, plant materials or combinations thereof.

8. The method of claim 6, wherein the ethylene glycol is derived from petrochemicals.

9. The method of claim 6, wherein the ethylene glycol is derived from biomass.

10. The method of claim 6, further comprising solid-state polymerizing the bio-PET polymer into a bio-PET resin.

11. The method of claim 10 further comprising processing the bio-PET resin into a bio-PET preform or bio-PET packaging.

12. The method of claim 11, wherein the bio-PET packaging is a food or beverage container or product.

13. The method of claim 12, wherein the food container is selected from the group consisting of disposable or reusable containers.

14. The method of claim 12, wherein the beverage container is a bottle or cup.

15. The method of claim 12, wherein the food product is selected from the group consisting of straws, toothpicks, disposable plates and disposable cutlery.

16. The method of claim 1, wherein dehydrocyclizing bio-3,6-dimethylcyclohex-1-ene to bio-p-xylene is carried out at a temperature from 300° C. to 650° C.

17. The method of claim 1, wherein dehydrocyclizing bio-3,6-dimethylcyclohex-1-ene to bio-p-xylene is carried out at atmospheric pressure.

* * * * *